United States Patent
Deck et al.

(10) Patent No.: US 8,853,444 B2
(45) Date of Patent: Oct. 7, 2014

(54) PROCESSES FOR PREPARING 4-CHLOROBENZENESULFONIC ACID AND 4,4'-DICHLORODIPHENYL SULFONE

(75) Inventors: Patrick Deck, São Paulo (BR); Heiner Schelling, Kirchheim (DE); Florian Garlichs, Neustadt (DE)

(73) Assignee: BASF SE (DE)

( * ) Notice: Subject to any disclaimer, the term of this patent is extended or adjusted under 35 U.S.C. 154(b) by 689 days.

(21) Appl. No.: 13/041,536

(22) Filed: Mar. 7, 2011

(65) Prior Publication Data

US 2011/0218357 A1    Sep. 8, 2011

Related U.S. Application Data

(60) Provisional application No. 61/310,723, filed on Mar. 5, 2010.

(51) Int. Cl.
*C07C 315/00* (2006.01)
*C07C 303/22* (2006.01)

(52) U.S. Cl.
CPC ............. *C07C 303/22* (2013.01); *C07C 315/00* (2013.01)
USPC ........................................................ 562/83

(58) Field of Classification Search
USPC ........................................................ 562/83
See application file for complete search history.

(56) References Cited

U.S. PATENT DOCUMENTS

| | | | |
|---|---|---|---|
| 2,492,706 A | 12/1949 | McCann et al. | |
| 2,593,001 A | 4/1952 | Bender et al. | |
| 2,805,126 A | 9/1957 | Jones | |
| 2,820,697 A | 1/1958 | Peirce | |
| 2,971,985 A | 2/1961 | Joly et al. | |
| 3,855,312 A * | 12/1974 | Horner ............................ | 568/34 |
| 4,016,210 A | 4/1977 | Horner et al. | |
| 4,873,372 A | 10/1989 | Schaefer et al. | |
| 4,876,390 A | 10/1989 | McCulloch | |
| 4,937,387 A | 6/1990 | Steiner et al. | |
| 5,082,973 A | 1/1992 | Stumpp et al. | |
| 2011/0263902 A1 | 10/2011 | Deck et al. | |
| 2011/0263903 A1 | 10/2011 | Deck et al. | |

FOREIGN PATENT DOCUMENTS

| | | |
|---|---|---|
| DE | 2252571 A1 | 5/1974 |
| EP | 279387 A1 | 8/1988 |
| EP | 0381049 A1 | 8/1990 |
| GB | 735836 A | 8/1955 |
| GB | 1393929 A | 5/1975 |

* cited by examiner

*Primary Examiner* — Sudhakar Katakam
*Assistant Examiner* — Kofi Adzamli
(74) *Attorney, Agent, or Firm* — Drinker Biddle & Reath LLP

(57) ABSTRACT

Processes for preparing 4-chlorobenzenesulfonic acid from 2-chlorobenzenesulfonic acid and/or 3-chlorobenzenesulfonic acid, which processes include the conversion of 2-chlorobenzenesulfonic acid and/or 3-chlorobenzenesulfonic acid to 4-chlorobenzenesulfonic acid in the presence of sulfuric acid at a temperature of 100 to 300° C.; as well as processes for preparing 4,4'-dichlorodiphenyl sulfone, which include such described processes for preparing 4-chlorobenzenesulfonic acid.

11 Claims, No Drawings

PROCESSES FOR PREPARING 4-CHLOROBENZENESULFONIC ACID AND 4,4'-DICHLORODIPHENYL SULFONE

CROSS-REFERENCE TO RELATED APPLICATIONS

This application claims benefit under 35 U.S.C. §119(e) of U.S. Provisional Application 61/310,723, filed Mar. 5, 2010.

BACKGROUND OF THE INVENTION 4,4'-Dichlorodiphenyl sulfone is used especially as a monomer in the synthesis of polyarylene ether sulfones. Examples of commercial significance are polyether sulfone (polymerization of 4,4'-dihydroxydiphenyl sulfone with 4,4'-dichlorodiphenyl sulfone), polysulfone (polymerization of bisphenol A with 4,4'-dichlorodiphenyl sulfone) and polyphenylene sulfone (polymerization of 4,4'-dihydroxybiphenyl with 4,4'-dichlorodiphenyl sulfone). 4,4'-Dichlorodiphenyl sulfone is thus a central unit for the preparation of these industrial polymers.

A preferred reactant fo the preparation of polyarylene ether sulfones is high-purity 4,4'-dichlorodiphenyl sulfone, since exclusively the 4,4' isomer forms linear, nonangular polymers which have the desired product properties, for example chemical and thermal stability, high dimensional stability and flame retardancy.

Processes for preparing 4,4'-dichlorodiphenyl sulfone are known from the prior art. The known processes comprise especially the preparation proceeding from monochlorobenzene and a sulfonating agent via 4-chlorobenzenesulfonic acid as an intermediate, which is generally not isolated.

DE 2252571 describes the synthesis of dichlorodiphenyl sulfone from monochlorobenzene and sulfuric acid at temperatures of 220 to 260° C. in a pressure reactor and with removal of the water of reaction formed.

U.S. Pat. No. 2,593,001 describes a continuous process for preparing diaryl sulfones by reacting aromatic sulfonic acids with aromatics, wherein the water of reaction is removed continuously from the reaction zone by the aromatic compound added in gaseous form in countercurrent.

U.S. Pat. No. 2,971,985 discloses the synthesis of dichlorodiphenyl sulfone using $SO_3$, dimethyl sulfate and monochlorobenzene.

The syntheses to prepare dichlorodiphenyl sulfone form not only the desired 4,4'-dichlorodiphenyl sulfone, but different amounts of the 2,4'- and 3,4'-isomers are always obtained, which are referred to hereinafter collectively as incorrect isomers of 4,4'-dichlorodiphenyl sulfone. In order to arrive at a 4,4'-dichlorodiphenyl sulfone usable in polymerizations, it has to be isolated in very pure form (typically >99.0% by weight).

Mixtures of dichlorodiphenyl sulfone isomers can be worked up, for example, by crystallization with/from alcohols, such that increased purities of the desired 4,4'-dichlorodiphenyl sulfone are obtained. EP-A 279387 describes this type of purification by recrystallization.

A further means of removing the incorrect isomers is the chromatographic separation, described in U.S. Pat. No. 4,876,390, of the isomer mixture.

The whereabouts of the undesired incorrect isomers of 4,4'-dichlorodiphenyl sulfone, which are unsuitable for the polymerization, and of the by-produced isomers of monochlorobenzenesulfonic acids, i.e. 2-chlorobenzenesulfonic acid, 3-chlorobenzenesulfonic acid and 4-chlorobenzenesulfonic acid, are not mentioned in any case.

In principle, the undesired isomers can be discarded after discharge from the process. This can be done by discharging a portion of the mother liquor of the crystallization or after removal of the incorrect isomers from the mother liquor. Both reduce the yield of the process based on the feedstocks considerably. Moreover, disposal costs additionally arise. In this context, the aspect of environmental protection (correct disposal of chlorinated aromatics) cannot be neglected.

There is thus a considerable interest in not discarding incorrect isomers from the dichlorodiphenyl sulfone synthesis but in converting them to 4,4'-dichlorodiphenyl sulfone, in order thus to increase the yield.

Isomerization reactions proceeding from aryl sulfones are known per se from the prior art. In Zhurnal Organicheskoi Kimii, 1976, 12 (2), 397, and 1976, 13 (6), 1204, V.A. Kozlov et al. report the isomerization and splitting of tolyl phenyl sulfones and xylyl phenyl sulfones in 92.3% sulfuric acid. However, a conversion of the incorrect isomers from the dichlorodiphenyl sulfone synthesis to 4,4'-dichlorodiphenyl sulfone is not possible in this way.

BRIEF SUMMARY OF THE INVENTION

The invention relates to a process for preparing 4-chlorobenzenesulfonic acid from 2-chlorobenzenesulfonic acid and/or 3-chlorobenzenesulfonic acid, comprising the conversion of 2-chlorobenzenesulfonic acid and/or 3-chlorobenzenesulfonic acid to 4-chlorobenzenesulfonic acid in the presence of sulfuric acid at a temperature of 100 to 300° C.

The present invention further relates to a process for preparing 4,4'-dichlorodiphenyl sulfone, comprising said process for preparing 4-chlorobenzenesulfonic acid.

It was an object of the present invention to provide a process for preparing 4,4'-dichlorodiphenyl sulfone which has the aforementioned disadvantages to a lesser degree, if at all.

More particularly, the yield of the known processes for preparing 4,4'-dichlorodiphenyl sulfone should be increased by converting 2,4' and/or 3,4'-dichlorodiphenyl sulfone formed as a by-product to 4,4'-dichlorodiphenyl sulfone.

The aforementioned objects are achieved by the process according to the invention for preparing 4-chlorobenzenesulfonic acid and by the process according to the invention for preparing 4,4'-dichlorodiphenyl sulfone. Preferred embodiments can be inferred from the claims and the description which follow. Combinations of preferred embodiments do not leave the scope of the present invention.

The process for preparing 4,4'-dichlorodiphenyl sulfone from monochlorobenzene comprises the process for preparing 4-monochlorobenzenesulfonic acid from 2-chlorobenzenesulfonic acid and/or 3-chlorobenzenesulfonic acid.

The process according to the invention for preparing 4-monochlorobenzenesulfonic acid from 2-chlorobenzenesulfonic acid and/or 3-chlorobenzenesulfonic acid comprises the conversion of 2-chlorobenzenesulfonic acid and/or 3-chlorobenzenesulfonic acid to 4-chlorobenzenesulfonic acid in the presence of sulfuric acid at a temperature of 100 to 300° C.

The individual steps of the process according to the invention for preparing 4-monochlorobenzenesulfonic acid from 2-chlorobenzenesulfonic acid and/or 3-chlorobenzenesulfonic acid, and of the process according to the invention for preparing 4,4'-dichlorodiphenyl sulfone from monochlorobenzene, are explained hereinafter.

DETAILED DESCRIPTION OF THE INVENTION

Process for preparing 4-chlorobenzenesulfonic acid:
Monochlorobenzenesulfonic acid may be present in the form of 2-chlorobenzenesulfonic acid, 3-chlorobenzenesulfonic acid or 4-chlorobenzenesulfonic acid, or as a mixture of two or three of the aforementioned compounds. A mixture comprising at least two of the aforementioned isomers is referred to in the context of the present invention as an isomer mixture of monochlorobenzenesulfonic acid.

The present invention can be performed proceeding from 2-chlorobenzenesulfonic acid or proceeding from 3-chlorobenzenesulfonic acid, preference being given to the conversion proceeding from 2-chlorobenzenesulfonic acid. Likewise preferred is the performance of the process proceeding from a mixture comprising 2-chlorobenzenesulfonic acid and 3-chlorobenzenesulfonic acid and optionally 4-chlorobenzenesulfonic acid, i.e. proceeding from an isomer mixture.

The process may additionally also be performed proceeding from a mixture of 4-chlorobenzenesulfonic acid on the one hand, and 2-chlorobenzenesulfonic acid and/or 3-chlorobenzenesulfonic acid on the other hand. Particular preference is given to the conversion proceeding from an isomer mixture of monochlorobenzenesulfonic acid comprising 2-chlorobenzenesulfonic acid.

When the conversion proceeds from an isomer mixture of monochlorobenzenesulfonic acid comprising 4-chlorobenzenesulfonic acid, it is performed with an increase in the proportion of 4-chlorobenzenesulfonic acid in the isomer mixture.

According to the invention, the temperature in the course of conversion is from 100 to 300° C. The inventive temperature can be established in different ways. More particularly, the monochlorobenzenesulfonic acid and sulfuric acid starting compounds can be mixed at the appropriate temperature. More particularly, it is also possible to prepare a mixture at a temperature below the conversion temperature, and then to heat this mixture. What is essential to the invention is the attainment of a temperature within the range from 100 to 300° C.

The temperature influences the selectivity and the rate of formation of 4-chlorobenzenesulfonic acid. The temperature of the conversion is preferably from 150° C. to 250° C., especially from 170° C. to 210° C., more preferably from 180 to 200° C. Within the ranges mentioned, the selectivity of formation of 4-chlorobenzenesulfonic acid is particularly high. At the same time, the rate of formation is sufficiently high.

The duration of the conversion can vary over a wide period. The duration of the conversion is understood to mean that time within which the inventive conditions are met. The duration of the conversion is preferably from 5 minutes to 12 hours, especially from 15 minutes to 3 hours, more preferably from 30 minutes to 2 hours.

The amount of the sulfuric acid used can vary over a wide range. However, it has been found to be advantageous with regard to the yield of 4-chlorobenzenesulfonic acid when the molar ratio of sulfuric acid to monochlorobenzenesulfonic acid is at least 1. The sulfuric acid is preferably used in a molar ratio to the amount of monochlorobenzenesulfonic acid of 1 to 100, especially of 2 to 20, more preferably of 3 to 15.

The concentration of the sulfuric acid used is preferably from 75 to 93% by weight, especially from 80 to 90% by weight, more preferably from 83 to 87% by weight, based on the total weight of the sulfuric acid used. Compliance with these concentration ranges leads to a high yield of 4-chlorobenzenesulfonic acid and to a sufficiently high reaction rate. As usual, the percentages by weight of the sulfuric acid should be understood relative to the total weight of sulfuric acid and water present in the sulfuric acid. The difference to 100% by weight thus arises from water, the presence of which in the range specified promotes the formation of 4-chlorobenzenesulfonic acid.

It is preferred when the conversion in the context of the present invention is performed in the sulfuric acid. This conversion is performed in the liquid phase in sulfuric acid. In a preferred embodiment, the conversion is performed in the absence of other liquid compounds than the sulfuric acid and the starting compounds. This allows an undesired dilution of the sulfuric acid and reduction in the activity to be avoided.

The conversion is preferably performed with intensive mixing. Useful methods of mixing include all customary processes, especially stirring. The mixing can be performed before and/or during the conversion. In addition, all processes known to those skilled in the art for performing conversions in the liquid phase are useful for the performance of the conversion, though the reaction conditions should be taken into account with regard to the selection of the materials of a reactor. Preferred embodiments for performing the reaction are stirred tank reactors or static mixers with downstream delay reactor.

Process for preparing 4,4'-dichlorodiphenyl sulfone:

In one embodiment of the invention, the described process for preparing 4-chlorobenzenesulfonic acid is integrated into a process for preparing 4,4'-dichlorodiphenyl sulfone proceeding from monochlorobenzene. This increases the yield of the process for preparing 4,4'-dichlorodiphenyl sulfone.

The present invention therefore provides a process for preparing 4,4'-dichlorodiphenyl sulfone proceeding from monochlorobenzene, comprising the process according to the invention for preparing 4-chlorobenzenesulfonic acid. It is possible to integrate all preferred embodiments described in the context of the process for preparing 4-chlorobenzenesulfonic acid advantageously into the process for preparing 4,4'-dichlorodiphenyl sulfone. The only prerequisite is that the process for preparing 4,4'-dichlorodiphenyl sulfone proceeds via 4-chlorobenzenesulfonic acid as an intermediate.

In the course of the conversion, all processes for preparing 4,4'-dichlorodiphenyl sulfone from monochlorobenzene, which proceed via 4-chlorobenzenesulfonic acid as an intermediate, form a mixture of the desired 4,4'-dichlorodiphenyl sulfone with at least one incorrect isomer, but typically each of the two incorrect isomers, 2,4'-dichlorodiphenyl sulfone and 3,4'-dichlorodiphenyl sulfone, and also typically 2-chlorobenzenesulfonic acid, 3-chlorobenzenesulfonic acid and/or 4-chlorobenzenesulfonic acid.

In a preferred embodiment, the process for preparing 4,4'-dichlorodiphenyl sulfone comprises at least the following steps:

(a) converting monochlorobenzene to a mixture comprising 4,4'-dichlorodiphenyl sulfone and at least one compound selected from 2,4'-dichlorodiphenyl sulfone and 3,4'-dichlorodiphenyl sulfone, forming 4-chlorobenzenesulfonic acid as an intermediate, (b) at least partially removing 4,4'-dichlorodiphenyl sulfone from the mixture obtained in step (a), (c) splitting 2,4'-dichlorodiphenyl sulfone and/or 3,4'-dichlorodiphenyl sulfone and optionally 4,4'-dichlorodiphenyl sulfone in the presence of sulfuric acid, (d) simultaneously or subsequently converting the isomer mixture of monochlorobenzenesulfonic acids obtained in step (c) to 4-chloro-benzenesulfonic acid by the process according to the invention for preparing 4-chlorobenzenesulfonic acid from 2-chlorobenzenesulfonic acid and/or 3-chlorobenzenesulfonic acid, and (e) at least partially recycling the 4-chlorobenzenesulfonic acid obtained in step (d) with renewed conversion according to step (a).

The above step (a) relates to the conversion of monochlorobenzene to a mixture of 4,4'-dichlorodiphenyl sulfone and at least one compound selected from 2,4'-dichlorodiphenyl sulfone and 3,4'-dichlorodiphenyl sulfone. In principle, all known processes for preparing 4,4'-dichlorodiphenyl sulfone which proceed from monochlorobenzene and via 4-chlorobenzenesulfonic acid as an intermediate are useful in the context of the process according to the invention. Corresponding processes are known to those skilled in the art.

Typically, monochlorobenzene is reacted with a sulfonating agent to form 4-chlorobenzenesulfonic acid. However, this unavoidably forms the incorrect isomers of monochlorobenzenesulfonic acid mentioned as fundamentally undesired by-products. Subsequently, the 4-chlorobenzenesulfonic acid and the 2-chlorobenzenesulfonic acid and/or 3-chlorobenzenesulfonic acid isomers are reacted with monochlorobenzene to give 4,4'-dichlorodiphenyl sulfone, which forms the incorrect isomers of dichlorodiphenyl sulfone mentioned. Monochlorobenzenesulfonic acid can also be formed as an intermediate which is not isolated.

In a preferred first embodiment, 4,4'-dichlorodiphenylsulfone is formed by reaction of 4-chlorobenzenesulfonic acid with monochlorobenzene in a countercurrent column, wherein the water of reaction is stripped out continuously via the top by the aromatic added in gaseous form in the bottom of the column. For the synthesis of 4,4'-dichlorodiphenyl sulfone, 4-chlorobenzenesulfonic acid or else sulfuric acid can be added at the top of the column. The latter reacts in the column with monochlorobenzene first to give monochlorobenzenesulfonic acid, which then likewise reacts with monochlorobenzene to give dichlorodiphenyl sulfone. The corresponding process is described, for example, in U.S. Pat. No. 2,593,001, the content of which is hereby fully incorporated.

In a second preferred embodiment, dichlorodiphenyl sulfone is prepared using $SO_3$, dimethyl sulfate and monochlorobenzene. This involves first allowing $SO_3$ to react with dimethyl sulfate in a molar ratio of 2 to 1 under moderate conditions. In the course of this, a portion of the $SO_3$ reacts with dimethyl sulfate to form the corresponding pyrosulfate. The remaining $SO_3$ remains dissolved in the liquid formed. This mixture is subsequently mixed with monochlorobenzene at temperatures below 100° C. (2 mol of monochlorobenzene per 2 mol of $SO_3$ and 1 mol of dimethyl sulfate). The dissolved $SO_3$, the dimethyl pyrosulfate and the monochlorobenzene form 1 mol of dichlorodiphenyl sulfone and 2 mol of monomethyl sulfate. The reaction mixture is subsequently passed into water. Dichlorodiphenyl sulfone precipitates out. This is filtered off and dried. The corresponding process is described, for example, in U.S. Pat. No. 2,971,985, the content of which is hereby fully incorporated.

In the course of step (a), the workup of the reaction product or of the reaction products in a manner known to those skilled in the art may optionally follow. Workup is understood to mean the recovery and optionally purification of the 4,4'-dichlorodiphenyl sulfone. Corresponding processes are guided by the way in which step (a) is performed and are likewise known to those skilled in the art.

In one embodiment, the reaction mixture is separated by adding water and separating the two liquid phases which form. The aqueous phase comprises unconverted monochlorobenzenesulfonic acids. The water is evaporated off, and the monochlorobenzenesulfonic acid is recovered as a feedstock. Dichlorodiphenyl sulfone can subsequently be isolated from the organic phase, which consists predominantly of monochlorobenzene and dichlorodiphenyl sulfone. A corresponding process is described, for example, in U.S. Pat. No. 4,937,387, the content of which is hereby fully incorporated. For removal of the incorrect isomers of dichlorodiphenyl sulfone, see step (b).

The further reaction of 2-chlorobenzenesulfonic acid and/or 3-chlorobenzenesulfonic acid with monochlorobenzene leads to the formation of the undesired 2,4'-dichlorodiphenyl sulfone and/or 3,4'-dichlorodiphenyl sulfone isomers.

After step (a), 4,4'-dichlorodiphenyl sulfone is removed in the course of step (b).

The removal of 4,4'-dichlorodiphenyl sulfone is required since it already constitutes a majority of the end product ultimately obtained in accordance with the invention, which should be substantially removed from the further conversion in step (c). Steps (c) to (e) serve, inter alia, to increase the yield of step (a).

Corresponding processes for removing 4,4'-dichlorodiphenyl sulfone are known to those skilled in the art. As described above, the removal can be effected, for example, by chromatography. Preference is given to effecting the removal by crystallization as described, for example, in EP 279 387, the content of which is hereby fully incorporated.

It is preferred to supply the mixture comprising 2,4'-dichlorodiphenyl sulfone and/or 3,4'-dichlorodiphenyl sulfone, with or without 2-chlorobenzenesulfonic acid, 3-chlorobenzenesulfonic acid and/or 4-chlorobenzenesulfonic acid, which has been at least partially freed of 4,4'-dichlorodiphenyl sulfone, without further workup to step (c). In an alternative embodiment, it is, however, possible to remove 2-chlorobenzenesulfonic acid, 3-chlorobenzenesulfonic acid and/or 4-chlorobenzenesulfonic acid in an intermediate step and only to supply the incorrect isomers of 4,4'-dichlorodiphenyl sulfone to step (c), and to reuse the monochlorobenzenesulfonic acids removed in the process.

After step (b) and before performance of step (c), chlorobenzene is preferably removed. Corresponding processes for removing chlorobenzene are known to those skilled in the art, distillation being especially suitable. This can prevent undesired additional chlorobenzenesulfonic acid forming from monochlorobenzene owing to the further conversion.

Subsequently, in step (c), 2,4'-dichlorodiphenyl sulfone and/or 3,4'-dichlorodiphenyl sulfone is/are split in the presence of sulfuric acid to form an isomer mixture of monochlorobenzenesulfonic acids.

The sulfuric acid used in step (c) preferably has a concentration of 90 to 100% by weight, more preferably of 93 to 100% by weight, especially of 94 to 98% by weight, most preferably 96% by weight, based on the total weight of the sulfuric acid used. The conversion in the sulfuric acid is preferably effected in the liquid phase.

The temperature in step (c) may vary over a wide range. However, it is advantageous to perform the splitting with sulfuric acid at a temperature of at least 100° C. since the rate of splitting is otherwise too low. Step (c) is preferably performed at a temperature of 100° C. to 300° C., especially of 140° C. to 250° C., more preferably of 160° C. to 230° C.

In principle, the duration of the conversion in step (c) may vary over a wide period. The duration of the conversion is understood to mean that time within which the inventive conditions are met. The duration of the conversion is preferably from 5 minutes to 12 hours, especially from 15 minutes to 3 hours, more preferably from 30 minutes to 2 hours.

The amount of the sulfuric acid used may vary over a wide range. However, it has been found to be advantageous when the molar ratio of acid to dichlorodiphenyl sulfone is at least 1. Preference is given to using sulfuric acid in a molar ratio to the amount of dichlorodiphenyl sulfone of 1 to 100, especially of 2 to 20, more preferably of 3 to 15.

The conversion of step (c) is preferably effected with intensive mixing in suitable vessels and/or reactors. Correspronding methods are known to those skilled in the art and observe the present reaction conditions.

Simultaneously with or after step (c), in the course of step (d), the inventive conversion of the isomer mixture to 4-chlorobenzenesulfonic acid is effected. Corresponding embodiments have been described above. It is possible in principle to use all embodiments designated as preferred.

Step (d) is preferably performed after step (c) with adjustment of the reaction conditions. However, it is also possible in principle to perform step (d) and step (c) simultaneously. The conditions of step (c) are adjusted in the latter case such that the process according to the invention for preparing 4-monochlorobenzenesulfonic acid proceeding from 2-monochlorobenzenesulfonic acid and/or 3-monochlorobenzenesulfonic acid is performed simultaneously. In this case, the person skilled in the art selects the duration of the combined steps (c) and (d) correspondingly, by adding up the preferred reaction times mentioned. The simultaneous performance of steps (c) and (d) is equivalent to the sequential performance under identical conditions. In this case, it is required in accordance with the invention to perform the combined steps in the presence of sulfuric acid at a temperature of 100° C. to 300° C. Preferred embodiments have been explained in the context of the process for preparing 4-chlorobenzenesulfonic acid.

However, it is preferred first to perform step (c) and then step (d), the two steps having different reaction conditions. The transition to step (d) is then effected by altering the reaction conditions.

Preference is thus given to effecting a transition from step (c) to step (d) by adjusting the desired conditions proceeding from step (c) to the conditions required according to step (d). The adjustment of the conditions preferably relates to the concentration of the sulfuric acid which, in step (d), is preferably from 80 to 90% by weight, especially from 82 to 88% by weight, more preferably from 83 to 87% by weight. The concentration of the sulfuric acid used in step (c) is preferably from 90 to 100% by weight, more preferably from 93 to 100% by weight, especially from 94 to 97% by weight, most preferably 96% by weight. The concentration of the sulfuric acid is especially adjusted by diluting with water, i.e. adding water.

It is also possible in principle to isolate the reaction discharge resulting from step (c) and then to use it in step (d). However, it is preferred to perform step (d) after step (c).

In the course of step (e), the 4-chlorobenzenesulfonic acid obtained in step (d) is at least partially recycled, preferably after removal with renewed conversion according to step (a). Accordingly, the 4-chlorobenzenesulfonic acid obtained is used to increase the yield of 4,4'-dichlorodiphenyl sulfone.

4-Chlorobenzenesulfonic acid is preferably removed by extraction or precipitation and more preferably by crystallization.

The invention will now be described in further detail with reference to the following non-limiting examples.

EXAMPLES

Comparative Example 1

1 g (3.5 mmol) of 2,4-dichlorodiphenyl sulfone was suspended in 10 ml (18.4 g corresponding to 180 mmol) of concentrated sulfuric acid (96% by weight), and stirred at 170° C. for 3 h.

After a reaction time of 3 h, no dichlorodiphenyl sulfone, nor any monochlorobenzene, was present in the reaction discharge. According to HPLC analysis, the reaction product comprised a mixture of 2-, 3- and 4-chlorobenzenesulfonic acid. Instead of an isomerization, exclusively the splitting products of dichlorodiphenyl sulfone were obtained. An isomerization of dichlorodiphenyl sulfone is not possible in this way.

Comparative Example 2

1 g (3.5 mmol) of 2,4-dichlorodiphenyl sulfone and 1 g (3.5 mmol) of 3,4-dichlorodiphenyl sulfone were suspended in 4.8 g (42 mol) of 85% sulfuric acid and stirred at 190° C. for 13 h. According to HPLC analysis, a product mixture which was composed of 0.5% by weight of 2,4'-dichlorodiphenyl sulfone, 94.5% by weight of 3,4'-dichlorodiphenyl sulfone and 3.3% by weight of 4,4'-dichlorodiphenyl sulfone was obtained.

The main product was thus the undesired 3,4'-dichlorodiphenyl sulfone. 4,4'-Dichlorodiphenyl sulfone was formed only to a very minor degree.

Example 3

1 g (5.2 mmol) of 2-chlorobenzenesulfonic acid were suspended in 4.8 g (42 mmol) of 85% by weight sulfuric acid, and stirred at 190° C. The reaction was stopped after 10, 60 and 180 min by cooling and diluting with DMSO-$D_6$. The composition was determined by $^1$H NMR (results in Table 1).

TABLE 1

| Time | 2-CBSA | 4-CBSA |
|---|---|---|
| 0 h | 100% | 0% |
| 0.5 h | 55% | 45% |
| 1 h | 29% | 71% |
| 3 h | 3% | 97% |

(for Example 3, all figures in mol %)

Accordingly, proceeding from 2-chlorobenzenesulfonic acid in 3 equivalents of 85% sulfuric acid at 190° C., 4-chlorobenzenesulfonic acid was obtained without corresponding amounts of 3-chlorobenzenesulfonic acid being observed in the reaction discharge.

Recycling of incorrect isomers of 4,4'-dichlorodiphenyl sulfone is thus possible by splitting the incorrect isomers of 4,4'-dichlorodiphenyl sulfone and subsequently isomerizing the monochlorobenzenesulfonic acids with enrichment of 4-chlorobenzenesulfonic acid.

What is claimed is:

1. A process for preparing 4-chlorobenzenesulfonic acid from 2-chlorobenzenesulfonic acid and/or 3-chlorobenzenesulfbnic acid, comprising the conversion of 2-chlorobenzenesulfonic acid and/or 3-chlorobenzenesulfonic acid to 4-chlorobenzenesulfonic acid in the presence of sulfuric acid at a temperature of 100 to 300° C.

2. The process according to claim 1, wherein the conversion is effected. proceeding from an isomer mixture of monochlorobenzenesulfbnic acids comprising 2-chlorobenzenesulfonic acid and/or 3-chlorobenzenesulfonic acid and optionally 4-chiorobenzenesuifonic acid.

3. The process according to claim 1, wherein the conversion is effected proceeding from an isomer mixture of monochlorobenzenesulfonic acid comprising 2-chlorobenzenesulfonic acid.

4. The process according to claim 1, wherein the conversion is performed proceeding from an isomer mixture of monochlorobenzenesuifonic acid in the presence of 4-chlorobenzenesuifonic acid with an increase in the proportion of 4-chlorobenzenesulfonic acid in the isomer mixture.

5. The process according to claim 1. wherein the temperature of the conversion is from 150° C. to 250° C.

6. The process according to claim 1, wherein the sulfuric acid is used in a molar ratio to the amount of monochlorobenzenesulfonic acid of 1 to 100.

7. The process according to claim 1, wherein the sulfuric acid has a concentration of 80 to 90% by weight.

8. The process according to claim 1, wherein the conversion is performed over a period of 15 minutes to 3 hours.

9. The process according to claim 1, wherein the temperature of the conversion is from 170° C. to 210° C.

10. The process according to claim 1, wherein the sulfuric acid is used in a molar ratio to the amount of monochlorobenzenesulfonic acid of 2 to 20.

11. The process according to claim 1, wherein the sulfuric acid has a concentration of 83 to 87% by weight.

* * * * *